United States Patent [19]

Noerenberg et al.

[11] Patent Number: 4,802,476

[45] Date of Patent: Feb. 7, 1989

[54] ELECTRO-SURGICAL INSTRUMENT

[75] Inventors: Marc D. Noerenberg, Shakopee; Peter Stasz, Minneapolis, both of Minn.

[73] Assignee: Everest Medical Corporation, Brooklyn Center, Minn.

[21] Appl. No.: 56,434

[22] Filed: Jun. 1, 1987

[51] Int. Cl.$^4$ .............................................. A61B 17/39
[52] U.S. Cl. ........................ 128/303.14; 128/303.17; 604/22
[58] Field of Search ...................... 128/303.13–303.17, 128/303.19, 24 A; 604/22

[56] References Cited

U.S. PATENT DOCUMENTS

| 2,714,890 | 8/1955 | Vang | 128/24 A |
| 4,170,234 | 10/1979 | Graham | 128/303.14 |
| 4,674,458 | 6/1987 | Stasz | 128/303.14 |

Primary Examiner—Lee S. Cohen
Attorney, Agent, or Firm—Orrin M. Haugen; Thomas J. Nikolai; Frederick W. Niebuhr

[57] ABSTRACT

Described is a surgical tool having a unique blade comprised of a blank made of electrically conductive material, a first insulative member, a plurality of electrically conductive members laminated to the first and insulative member and a second insulative coating. The blade acts as a capacitive device or as a resistive device depending upon the precise configuration of the second insulative coating.

10 Claims, 4 Drawing Sheets

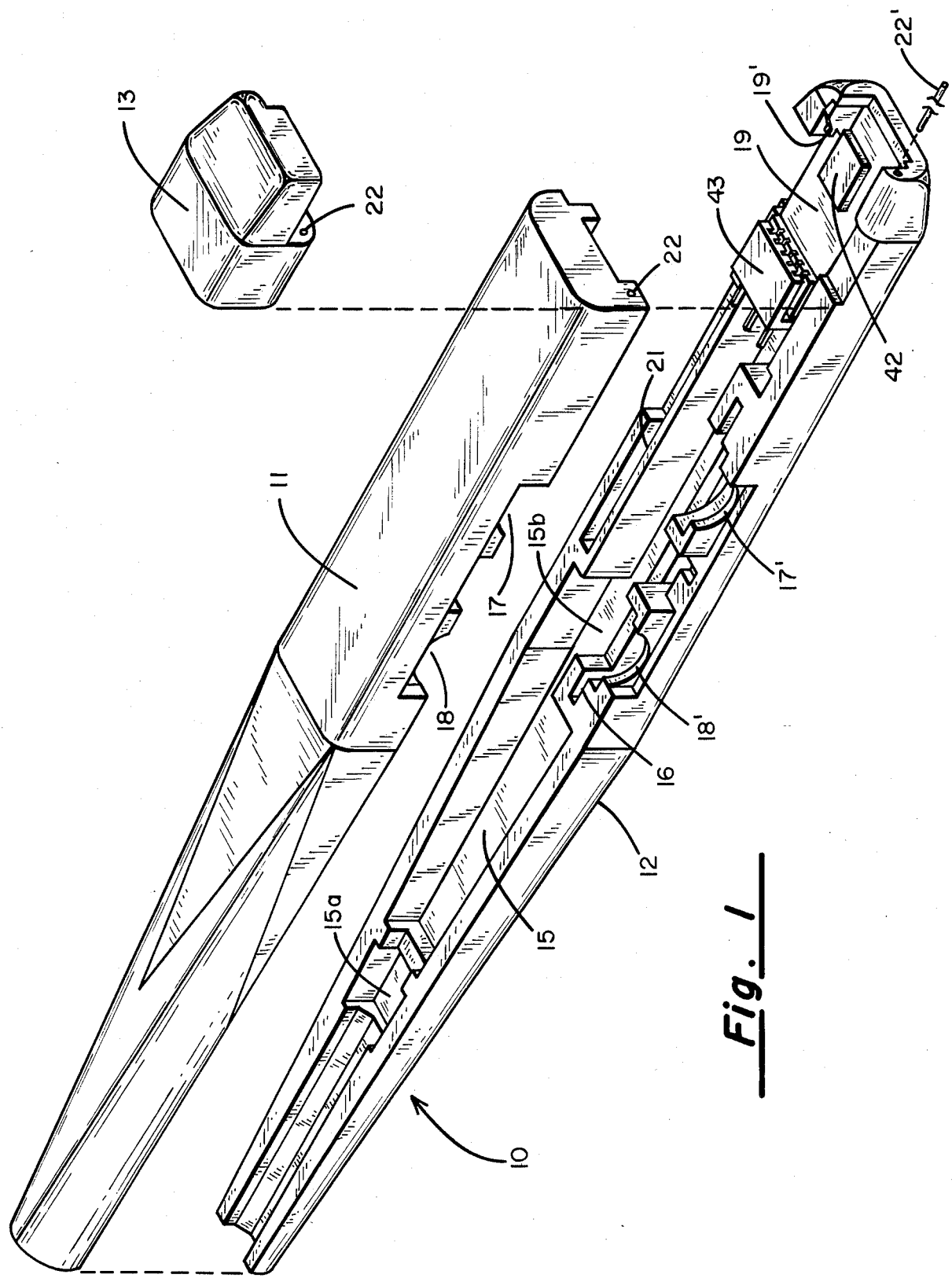

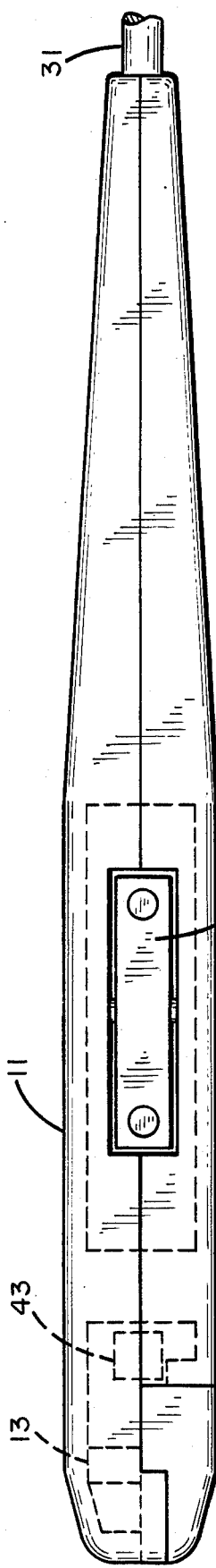
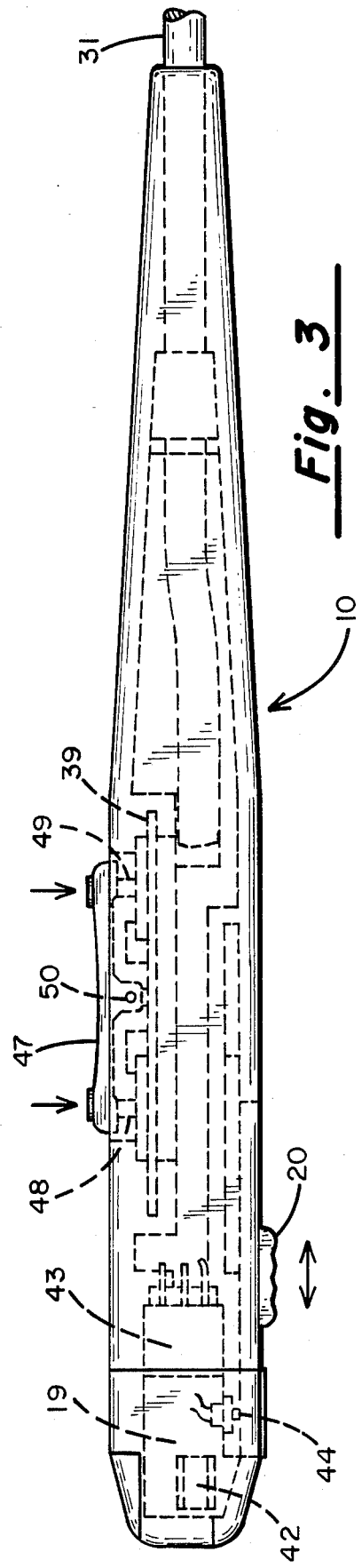
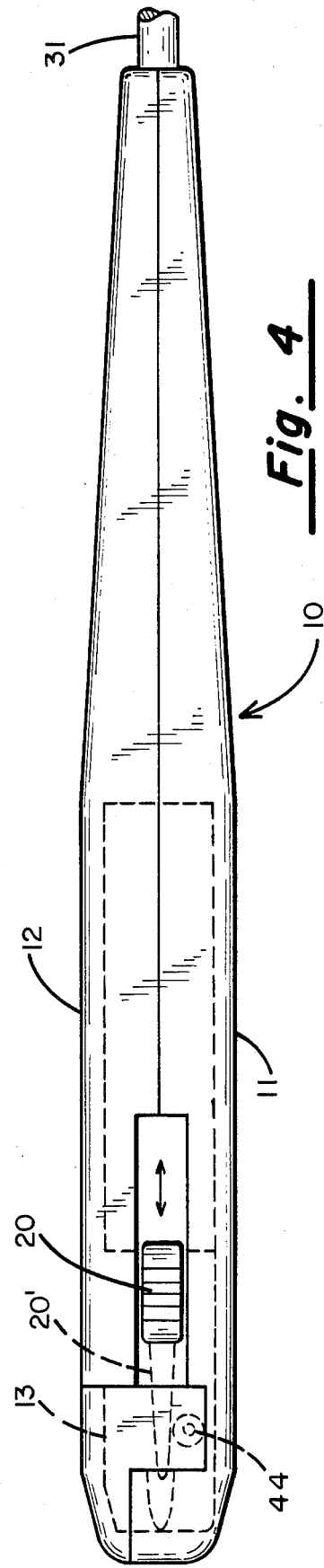

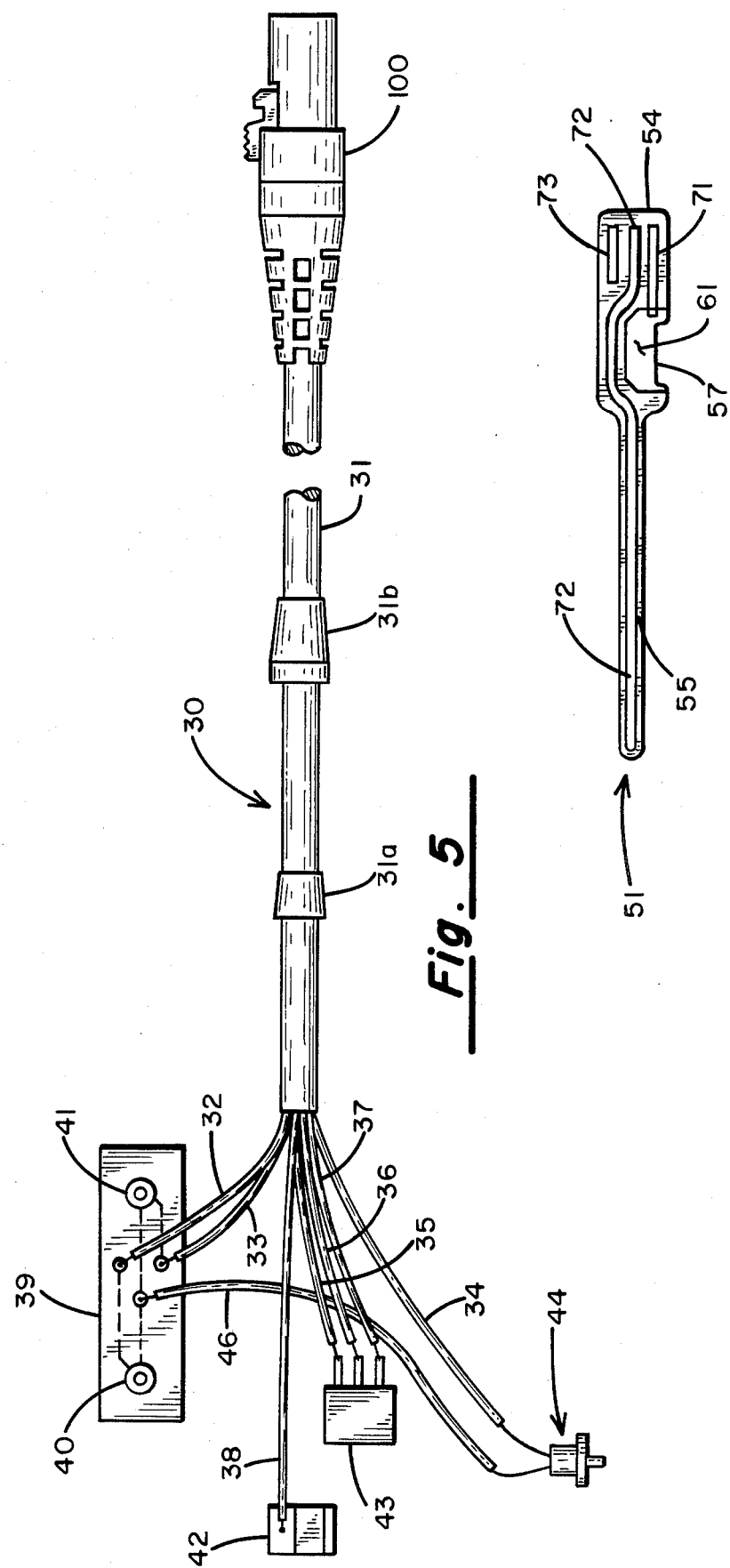

ELECTRO-SURGICAL INSTRUMENT

BACKGROUND OF THE INVENTION

I. Field of the Invention

The present invention relates to an electro-surgical instrument used for making incisions in tissue in which the blade is made to vibrate during use at a predetermined amplitude and frequency. The rapid, imperceptible movement of the blade results in cavitation at the blade'surface which frees it of the buildup of organic debris. More particularly, the present invention relates to a unique blade construction and blade holder for use in connection with such a tool.

II. Discussion of the Prior Art

As described in applicant's patent application Ser. No. 756,248 filed on July 18, 1985, now U.S. Pat. No. 4,674,498, various prior art electro-surgical blades have been less than effective since those blades either must be made of a special material, or must carry a considerably higher voltage which may cause undue tissue damage. Other prior art devices do not allow for proper coupling of the blade member to the voltage source and, therefore, tend to be ineffectual. Still other prior art blade and holder assemblies have extremely elaborate and complex electrical circuits which fail to accomplish a desirable result of an effective electro-surgical tool capable of operation in more than one mode.

One of the most severe problems in the prior art is the adhesion of charred tissue and blood to the blade which uncontrollably and erratically alters the impedance between the two blade energizing conductors and, therefore, renders the instrument almost useless as an effective cutting and/or electro-cautery device. The present invention provides an electro-surgical tool which, by utilizing state of the art semiconductor or printed circuit masking technology, can be designed to function as a standard surgical blade or as an electrified blade for cutting tissue and coagulating blood. The present invention also provides surgeons with an electro-surgical tool which can be used with either a capacitive blade or a resistive blade. The invention further provides means for locking either of the foregoing type of surgical blade in place with respect to a handle and for vibrating the blade so as to produce the desired cavitation effect for cleansing the blade continuously during use.

SUMMARY OF THE INVENTION

The purpose of the present invention is to provide an electro-surgical tool which can be utilized as a standard surgical cutting blade which mechanically cuts because of its sharpened edge when no electrical power is applied to it or, alternatively, as a bipolar electro-surgical blade for cutting and/or coagulating.

Another principal object of the present invention is to provide an electro-surgical tool utilizing a capacitive type bipolar blade in which the two conductors are separated by an insulator and driven by an alternating current.

Another principal object of the present invention is to provide an electro-surgery tool utilizing a resistive type blade.

Still another object of the present invention is to provide a blade holder which incorporates a transducer element for vibrating a blade secured therein sufficiently to produce a cavitation effect, thereby preventing adherence of tissue debris on the blade. The transducer is disposed in the handle member and in intimate contact with the blade so as to vibrate the blade producing cavitation at the interface between the tissue and blade.

In the two embodiments of the present invention described in detail below, the electro-surgical blade includes a blank made of a conductive material, such as stainless steel or the like. Alternatively, a ceramic blade may be used when suitably metallized as described in greater detail herein. The blank member may be formed with a sharpened edge leading to a point. Alternatively, the term blade is also applied to an unsharpened paddle as well. In each embodiment, when a conductive metal blank is used, a layer of insulative material is disposed on opposite sides of the blank over in the majority of its surface. Left exposed is the metal cutting edge and the bare metal area in which the transducer makes contact with the blade. Again, in both embodiments a plurality of conductive elements are laminated, deposited, or otherwise formed on the insulative layer discussed above. These conductive elements are intended to mate with corresponding conductors comprising electrical contacts located within the scalpel's handle. One of the contacts forms an electrical path to the uninsulated area intended to contact the transducer. A second conductor runs along the edge between the insulative material and the metal blank on one side of the blade. Another conductive element runs along the edge between the insulative material and the blank on the opposite side of the blade.

In one of the two embodiments discussed herein, another insulative coating is placed over the distal end portion of the blade. This layer prevents seepage of body fluids such as blood as well as other moisture along the blade into the body or handle of the cutting tool. Again, this second insulative layer does not cover the cutting edge of the blade or the major portion of the conductors. As a result, the blade of this embodiment can be characterized as a resistive blade in that it functions primarily due to heating caused by the passage of radio frequency current through the tissue between the two conductors.

In accordance with a second embodiment of the present invention, a second and outer insulative layer is included. The outer layer of insulative material in this embodiment is preferably made of Teflon ® plastic and covers the proximal portion of the blade. The Teflon plastic coating does generally cover a substantial portion of the conductive elements. For certain applications, it may also cover the sharp edge of the blade. In this second embodiment, the blade may be made to cut and/or coagulate due to the capacitive coupling of the R.F. energy to the tissue rather than the direct contact resistive coupling of the R.F. energy to the tissue.

DESCRIPTION OF THE DRAWINGS

FIG. 1 shows the body or handle portion for the scalpel of the present invention, the components shown in blown-apart form to reveal the interior design features;

FIG. 2 is a top view of the body or handle member for the scalpel;

FIG. 3 is a side view of the body or handle member for the scalpel;

FIG. 4 is an outside bottom view of the body or handle member for the scalpel;

FIG. 5 shows the wiring harness, a portion of which is located within the handle body;

FIG. 7 illustrates an electro-surgical paddle blade.

DESCRIPTION OF THE PREFERRED EMBODIMENT

Figure 6A:
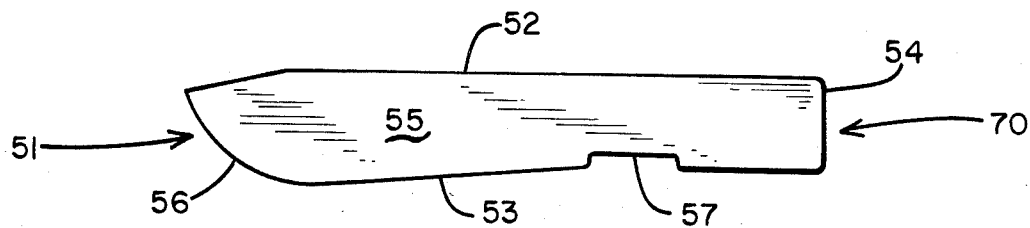
FIGS. 6a-6e shows one form of scalpel blade in accordance with the present invention during the various stages of its manufacture, FIG. 6a being the bare metal blank of the blade, FIG. 6b the metal blank with a first insulative coating over a major portion thereof, FIG. 6c the blank, the first insulative coating and a printed conductive layer thereon, FIG. 6d the second insulative layer covering a major portion of the conductive layer of the blade, and FIG. 6e an alternative second insulative layer formed on the blade.

FIGS. 1-4 are intended to disclose in detail the construction of the body or handle portion 10 of the electro-surgical scalpel system of the present invention. The body 10 is designed to serve as a holder for the blade and also retains the electrical assembly 30 including the blade socket or connector 43, and the blade 70 in assembled relation when the scalpel is in use.

As best shown in FIG. 5, the electrical assembly 30 includes an insulated cable sheath 31 containing seven separately insulated wires 32-38, a switch assembly 39 comprised of a pair of so-called push-button dome switches 40 and 41, a transducer 42, a blade socket 43, and one interlock switch 44 which is present to prevent operation of the electro-surgical scalpel unless the blade is completely and properly locked in place within the handle. One end of each of wires 32-38 of cable 31 is connected through a jack 100 to an electro-surgical generator apparatus (not shown) which provides the necessary R.F. power allowing the scalpel to be operated in any one of several modes determined by the mode selection switches 40 and 41 on the scalpel body.

As shown in FIG. 5, wire 32 is connected to one side of dome switch 40 which is used to control the cut function of the scalpel. Wire 33 is similarly connected to one side of the dome switch 41 which controls the coagulation function of the scalpel. A wire 46 is connected to one side of push-button switch 40. The other side of push-button switch 40 is connected to wire 34.

Wires 35, 36 and 37 are connected to individual terminals of the blade socket 43. The blade socket 43 is designed so that it will simply plug in to a recess molded into the handle and will be retained therein. Similarly, wire 38 is connected to the transducer 42. Transducer 42 is preferably a piezo-electric crystal which, when driven by an alternating current signal of an appropriate frequency, will develop a mechanical movement. As will be discussed in greater detail below, the presence of the blade properly locked in position in its holder is necessary to complete the electrical circuits used to power the scalpel.

As is best shown in FIG. 1, the scalpel body 10 is preferably molded from plastic and includes a first side portion 11, a second side portion 12, and a hinged cover member 13. FIG. 1 also shows the location of blade connector 43 when installed in the handle. The first an second side members 11 and 12 each contain a main channel 15 which, when the side members are brought together and bonded to one another, are designed to surround and contain a portion of the cable 31.

Similarly, members 11 and 12 include slots 16 for encompassing opposed side edges of the printed circuit switch assembly 39 to hold same in place. To enable access to the dome switches 40 and 41, members 11 and 12 each have a pair of semi-circular openings 17 and 18. As shown in FIGS. 1, 2 and 3, when members 11 and 12 are bonded together following insertion of the internal components, including the cable 30, the dome switch assembly 39, the blade socket 43 and the piezo-electric transducer 42, the semi-circular openings 17 and 18 of member 11 and the corresponding openings 17' and 18' of member 12 together form circular openings through which the plunger posts 48 and 49 of a toggle type switch actuator 47 extend to cooperate with the dome switches 40 and 41 on printed circuit board 39. The switch actuator 47 pivots about a centrally disposed, transversely extending pin 50 when pressed on either end thereof as indicated by the small arrows.

Another important feature of the blade handle 10 is the inclusion of a molded insert 19, which supports connector 43 thereon and which is adapted to fit within a cavity formed in the interior of the handle "half" 12. It includes a boss 19' which, in conjunction with the rotatable cover 13 and the sliding latch mechanism 20, captures the blade, preventing it from being pulled out of its electrical engagement with the blade connector 43 or its electrical and mechanical engagement with the electrical-to-mechanical transducer 42. More particularly, the boss or projection 19' on insert 19 engages a notch 57 in the blade and prevents the blade from rocking in or being pulled free of the handle 10 during a surgical cutting or coagulation procedure.

As already mentioned, the locking mechanism includes a slidable latch member 20 (shown in FIG. 4) which is retained in place by virtue of being disposed in the latch slots 21 (shown in FIG. 1). When the hinged cover 13 of the body 10 is fully closed and the latch member 20 is moved to its locked position, the forward projecting nose 20' of the latch member 20 passes through a groove or recess formed in the bottom surface of the cover member 13 to secure the hinged cover and prevents it from rotating about its hinge pin 22' which, as indicated in FIG. 1, is inserted in holes 22 in cover member 13 and handle member 12. Also, when in the locked position, switch 44 is activated making an electrical connection between wires 34 and 46 completing a circuit between the common point of the two dome switches and the generator (not shown). When the lock slide member 20 is slid out of the locked position, the cover member 13 is free to swing open for blade removal, braking the electrical connection between wires 34 and 46, thus precluding operation of the scalpel in an unlocked position.

To provide a desired strain relief ad to positively couple the handle member 10 to the cable 30, the cable 30 includes enlarged collars 31(a) and 31(b) which fit into recesses 15(a) and 15(b) molded internally of the handle portions 11 and 12.

An important aspect of the present invention is the unique design of a bipolar blade which cooperates with the body or handle 10 and electrical assembly 30 discussed above. Embodiments of this novel and unique blade are shown in its various stages of manufacture in FIGS. 6a-6e and in FIG. 7.

As shown in FIG. 6a, in accordance with one embodiment of the present invention, the first step in constructing the blade 70 is to form a metal blank 51 to a desired shape. Blank 51 has a top edge 52, a bottom edge 53, and back or proximal edge 54, a front face surface 55 and an opposed rear face. The bottom edge 53 is curved near its distal end 56, the curve meeting the top edge 52 at a point. The bottom edge 53 also includes a rectangular shaped notch 57 which, when the scalpel is assembled, mates with the boss 19' on the insert 19 internal of the distal end portion of the handle 10 to prevent the blank 51 from sliding or rocking vertically within the handle during cutting. The bottom edge 53 may be honed to a sharp cutting edge.

Figure 6B:
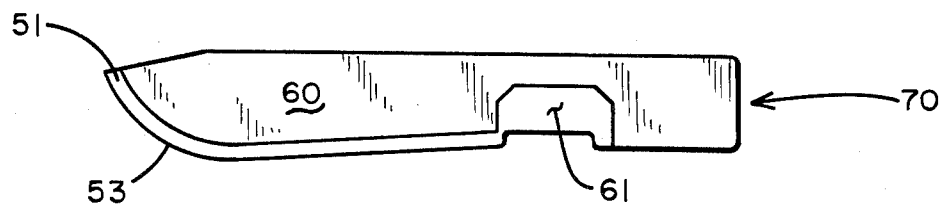
Figure 6C:
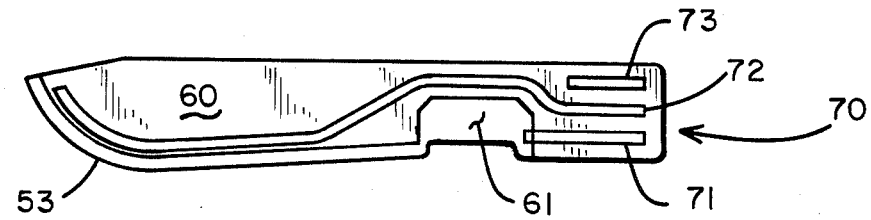

FIG. 6b shows the next step in constructing the blade. Added to the blank 51 is an insulative coating 60 which covers a substantial part of the blank 51. Left exposed is the lower sharpened edge 53 which is used for cutting. Also left exposed is a portion 61 which is dimensioned to contact the transducer 42 when the blade is properly seated within its handle. By leaving the bare metal portion 61 uninsulated, an alternating electrical current can be made to pass through the blade and the abutting transducer and back to the generator via conductor 38 in the cable 30.

The next step in the blade construction process (shown in FIG. 6c) is to laminate or chemically deposit electrical conductors 71, 72, and 73 on the insulative coating 60 in accordance with a desired pattern which may be created using a masking technique. Electrical conductor 71 makes an electrical connection between the lowermost conductor of blade connector 43 and the bare metal portion 61 of the blade which contacts the crystal transducer 42. Conductor 72 is intended to make an electrical connection with the middle conductor of blade connector 43. As shown FIG. 6c, conductor 72 is patterned to run along the front face surface 55 of the blade on top of the insulative layer 60 near the cutting edge 53. Similarly, conductor 73 is intended to make an electrical connection with the top conductor of blade connector 43. Conductor 73 has a shape similar to conductor 72 and runs in a similar path along the back surface of the blade on top of the insulative layer 60.

Figure 6D:
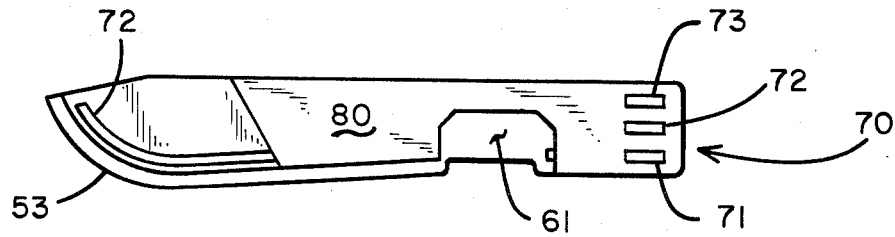

The final element of a first embodiment of a blade is shown in FIG. 6d. In this step, a second insulative layer 80 is deposited or otherwise placed over a predetermined proximal portion of the blade. The purpose of layer 80 is to cooperate with the walls defining the front slot opening in the handle 10 to prevent seepage of moisture into the handle 10 of the scalpel. Those skilled in the art will recognize that moisture inside the body of the scalpel could create an electrical short preventing proper operation of the scalpel. Also, it can lead to cleaning and sterilization difficulties. Left exposed is the portion 61 of the blank 51 which is intended to contact the transducer, the cutting edge 53, the portion of the conductive elements 72 and 73 which a in close proximity and parallel to the cutting edge 53, and the portions of the conductive members 71, 72 and 73 which mate with the conductive elements of the blade connector 43.

When the bipolar blade of FIGS. 6d or 7 is properly seated within its handle and energized in its cut mode by the generator (not shown), a substantial R.F. voltage is developed between the conductive strips 72 and 73 on opposed sides of the blade. When brought into contact with the tissue to be cut, a current passes through the tissue causing sufficient heating of the cells to cause them to rupture resulting in an incision. In the coagulation (coag) mode, the cells are dehydrated rapidly, cauterizing the wound to stem the flow of blood. As is explained in the aforereferenced patent application Ser. No. 756,248, the energization of the piezo-electric transducer results in cavitation which precludes buildup of tissue debris on the blade.

Figure 6E:
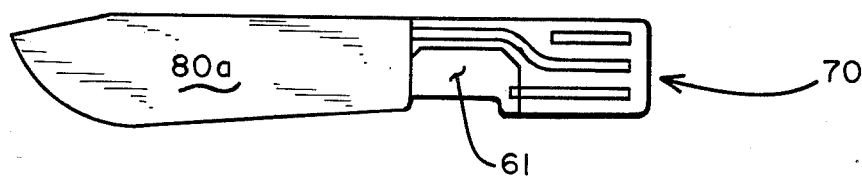

FIG. 6e illustrates a further optional manufacturing step which may be applied to the blade shown in FIG. 6d. In FIG. 6e the distal portion of the blade on both sides is treated with a Teflon ® coating. This Teflon coating 80a not only provides the requisite level of protection against infiltration of moisture, but also provides a smooth, stick-free surface. Even though the Teflon material covers the front and rear conductors 72 and 73 on the working portion of the blade, cutting occurs because, when appropriately energized by the R.F. power generator (not shown) to which the cable connector 100 is attached, the structure acts as a capacitor producing a low impedance path to the flow of R.F. current which then produces the cauterization of the tissue being cut. While FIG. 6e shows the entire front portion of the blade being coated with Teflon material, one could leave the cutting edge 53 of the blade exposed without eliminating the capacitive effect. In a similar fashion, the paddle blade of FIG. 7 may likewise be treated.

It is also contemplated that the blank 51 be fabricated from ceramic rather than metal and that the conductive pad area 61 and the conductive strips, such as strips 71, 72, and 73 be formed thereon in a chemical deposition, lamination or etching process using well known printed circuit techniques.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. An electro-surgical tool having a cutting mode of operation, coagulating mode of operating, switch means for altering the mode of operation between the cutting mode and the coagulating mode, a handle member, an improved blade, means associated with said handle member for retaining said blade in fixed registration with respect to said handle member while establishing an electrical connection with said switch means, electrical-to-mechanical transducer means for vibrating said blade at a pre-determined frequency and amplitude sufficient to create cavitation to prevent buildup of tissue and debris, and means for energizing the blade for cutting and coagulating, said improvements to the blade comprising of:

(a) a blank having two opposed side surfaces and a working edge along a pre-determined portion thereof, said blank having a notch cooperating with said means associated with said handle member for retaining said blade, said blank being made of a material having a conductive surface;

(b) a first insulative coating covering all of said blank except said working edge of said blank and a portion of the conductive surface of said blank which comes in contact with said electrical-to-mechanical transducer means;

(c) a first electrically conductive strip member disposed on said first insulative coating and having one end thereof leading to said portion of the conductive surface of said blank which comes in contact with said electrical-to-mechanical transducer means;

(d) a second electrically conductive strip member disposed on said first insulative coating on one side surface of said blank so as to be electrically insulated from the conductive surface of said blank, said second conductive strip member having a portion located near the working edge of said blank;

(e) a third electrically conductive strip member disposed on said first insulative coating on the side surface of said blank opposite said one side surface so as to be electrically insulated from the conductive surface of said blank, said third conductive strip member having a portion located near the working edge of said blank and generally parallel to said portion of said second conductive strip member; and (f) a second insulative coating deposited upon a predetermined portion of said blank for preventing passage of body fluids into said handle member during use.

2. The apparatus of claim 1 wherein said second insulative coating covers all but said working edge and said portions of the second and third conductive strip members near said working edge.

3. The apparatus of claim 1 wherein said second insulative coating is made of tetrafluoroethylene.

4. The apparatus of claim 2 wherein said second insulative coating covers those portions of the second and third conductive strip members near said working edge.

5. The apparatus of claim 1 wherein said working edge is honed to a cutting edge.

6. An electro-surgical implement comprising in combination:

(a) a blade member comprising a generally flat blank, said blank having first and second opposed major surfaces and a working edge, a distal end portion, an electrically conductive pad area, and a predetermined pattern of electrical conductors extending along said working edge on said opposed major surfaces and terminating in electrical contacts on said distal end portion of said blank;

(b) an elongated insulating handle member having a hollow cavity therein, a proximal end and a distal end, said handle member including a cover member hinged thereto at the distal end thereof for allowing movement of said cover member between an open and a closed disposition, said handle member including a molded insert member supporting an electrical connector and means for retaining said blade member in fixed registration with respect to said handle member when said blade member is inserted in said electrical connector;

(c) a blade vibrating element held by said insert member for contacting said electrically conductive pad area, said cover member including means for forcing said electrically conductive pad area against said blade vibrating element when said cover member is in said closed disposition; and (d) an electrical cable member having a plurality of conductors therein, a first portion of said electrical cable member being disposed in said hollow cavity, a second portion of said electrical cable member extending outwardly from said proximal end of said handle member and terminating in a connector, certain of said plurality of conductors in said electrical cable, member being electrically coupled by said connector to said predetermined pattern of electrical conductors on said blade member, said conductive pad area and said blade vibrating element.

7. The electro-surgical implement as in claim 6 and further including manually operable switch means affixed to said handle member and in circuit with selected ones of said plurality of conductors in said cable member.

8. The electro-surgical scalpel as in claim 6 and further including electrical interlock means for inhibiting energization of said predetermined pattern of electrical conductors when said cover member is in other than said closed disposition.

9. The electro-surgical scalpel as in claim 6 wherein said blank is formed from metal.

10. The electro-surgical scalpel as in claim 6 wherein said blank is formed from ceramic.

* * * * *